United States Patent [19]

Batie et al.

[11] 4,222,262
[45] Sep. 16, 1980

[54] HARDNESS TESTING APPARATUS

[75] Inventors: John N. Batie, Gateshead; Graham T. Relf, Newcastle-upon-Tyne; Geoffrey A. Wilkin, Cramlington, all of England

[73] Assignee: Vickers Limited, London, England

[21] Appl. No.: 961,605

[22] Filed: Nov. 17, 1978

[30] Foreign Application Priority Data

Nov. 25, 1977 [GB] United Kingdom ............ 49235/77

[51] Int. Cl.³ .......................................... G01N 3/48
[52] U.S. Cl. ................................................. 73/81
[58] Field of Search ............................ 73/81, 82, 83, 85

[56] References Cited

U.S. PATENT DOCUMENTS

| 3,754,436 | 8/1973 | Saxton | 73/81 |
| 3,822,946 | 7/1974 | Rynkowski | 73/81 X |
| 4,147,052 | 4/1979 | Tsujiuchi et al. | 73/81 |

*Primary Examiner*—Jerry W. Myracle
*Attorney, Agent, or Firm*—Larson, Taylor and Hinds

[57] ABSTRACT

Hardness testing apparatus, for use in assessing dimensions, from which a hardness value can be determined, of an indentation formed under controlled conditions in a surface of a specimen, having a photosensitive detector for sensing brightness over an image in which the indentation differs in brightness from the rest of the image. The detector produces electrical signals representative of sensed brightness. Discrimination circuitry discriminates signals representative of brightness within the indentation from signals representative of brightness outside the indentation. Correlation of discrimination results provides an assessment of indentation dimensions. Preferably oblique lighting is used to provide enhanced brightness differentation between a multifaceted indentation and other specimen surface features. The oblique light is directed so as to be specularly reflected from a facet of the indentation vertically with respect to the general specimen surface.

10 Claims, 17 Drawing Figures

HARDNESS TESTING APPARATUS

The present invention relates to hardness testing apparatus.

One well-known form of hardness test is the Vickers Hardness test. In the standard form of this test, a pyramidal diamond indenter of semi-angle 68° is impressed under a known load into the surface of the material whose hardness is to be tested, and the resulting indentation is examined under an optical microscope provided with movable shutters operating in the image plane of the objective lens. Screws are provided by means of which an operator can adjust the positions of the shutters. In use, the screws are adjusted until the edges of the shutters coincide with diagonally opposite corners of the enlarged image of the indentation, the image being orientated such that one diagonal is normal to the edges of the shutters. The shutter adjustment screws are connected to a mechanical counting device which indicates the distance of separation of the edges of the shutters. In this condition the distance of separation of the shutter edges is a measure of the length of the diagonal of the image, and this length is indicated on the mechanical counting device.

This measurement process is then repeated for the other diagonal of the image of the indentation, and the average value of the diagonal lengths of the indentation is calculated from the known magnification of the microscope and used in the equation:

$$HV = \frac{2F \sin 68°}{d^2}$$

where

HV is the Vickers hardness number,

F is the load applied through the indenter (kg), and d is the average diagonal length of the indentation (mm).

This method is widely accepted and can give reliable results for a range of materials, but it is time-consuming and relies for its accuracy on the care and skill of the operator and errors can arise due to operator fatigue.

According to the present invention there is provided hardness testing apparatus, for use in assessing dimensions of an indentation formed under controlled conditions in a region of a surface of a specimen whose hardness is to be tested, from which dimensions a hardness value for the specimen can be derived, the specimen comprising:

(a) imaging means for illuminating the region of the surface of the specimen in which the indentation is formed and for forming an image of that region in an image plane of the apparatus, in such a manner that areas of the image formed in the image plane that are within the image of the indentation differ in brightness from areas of the image formed in the image plane that are outside the image of the indentation;

(b) photo-sensitive detection means arranged at the image plane for sensing brightness levels at image areas distributed over the image formed in the image plane and operable to deliver electrical detection signals having electrical levels representative of the brightness levels at the image areas;

(c) discrimination circuitry connected to said photo-sensitive detection means for receiving such electrical detection signals, operable to distinguish those electrical detection signals of electrical levels consistent with their being representative of brightness level at image areas within the image of the indentation from those electrical detection signals of electrical levels consistent with their being representative of brightness levels at image areas outside the image of the indentation, and operable to provide discrimination signals which take a first level when received electrical detection signals are of a level consistent with their being representative of brightness at image areas within the image of the indentation, and which take a second level when received electrical detection signals are of a level consistent with their being representative of brightness at image areas outside the image of the indentation; and (d) correlation means arranged to receive the discrimination signals from said discrimination circuitry and operable, in dependence upon the correlation of discrimination signals of the first and second levels respectively in relation to respective different image areas of the image formed in the image plane, to derive therefrom an assessment of dimensions of the indentation.

The use of apparatus embodying the present invention can reduce operator fatigue, and thus errors due to operator fatigue, while maintaining a good level of accuracy.

Embodiments of the present invention employ, in the photosensitive detection means, opto-electronic devices having electrical characteristics which are dependent upon the intensity of illumination to which the devices are subjected. Such devices are well known and have been used in a variety of applications where their light-dependent characteristics can be used in conjunction with suitable electronic circuitry to produce electrical outputs for measurement and control purposes. A silicon photodiode, for example, displays increasing electrical conductance as light intensity incident thereon increases, and, when connected to a constant voltage d.c. supply such as a battery, the current which flows in the photo-diode is dependent upon the intensity of illumination falling upon the photodiode. This current variation may be amplified by electronic means and displayed on a suitable meter to give measurements of light intensity down to very low levels.

Photodiodes having the ability to detect low levels of light intensity can be used in hardness testing apparatus embodying this invention in which one or more such photodiodes used in the photosensitive detection means are located with their light-sensitive surfaces in the image plane of a microscope objective lens which microscope forms part of imaging means of the apparatus. In the image plane the image of the indentation in the surface of a specimen whose hardness value to be derived will normally be magnified at present. The photodiode(s) provided in such an embodiment of the present invention are of a size which is small compared with the expected size of magnified images of indentations to be examined. The output of an electronic amplifier circuit connected to a photodiode in the photosensitive detection means in an embodiment of the present invention will be dependent upon the position of that photodiode with respect to the image of an illuminated indentation being examined. When the imaging means of the apparatus are such that an indentation is illuminated vertically through the microscope objective lens, the image of the indentation appears essentially as a dark square against a lighter background, and the output of the amplifier circuit will be low when the photodiode is located within the image of the indentation, and high when it is located outside that image.

In preferred embodiments of the present invention however, a multifaceted indentation is not illuminated vertically, rather oblique or angled illumination is employed to provide images of indentations. That is to say, the indentations are not illuminated vertically but are illuminated with light directed on an angle to the vertical so as to highlight particular facets of the indentations. More particularly the indentation is illuminated with one or more parallel beams of light which are incident upon respective facets of the indentation at angles such that the or each beam is reflected specularly from the facet concerned along the vertical. This mode of illumination produces bright images of the facets of the indentation against a darker background, and can have important advantages as explained below.

For a better understanding of the present invention, and to show how the same may be carried into effect, reference will now be made, by way of example, to the accompanying drawings, in which.

Figure 1B:
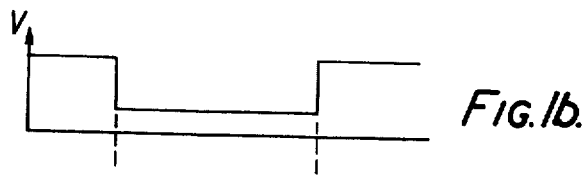
FIG. 1(b) is a waveform diagram.
Figure 1A:
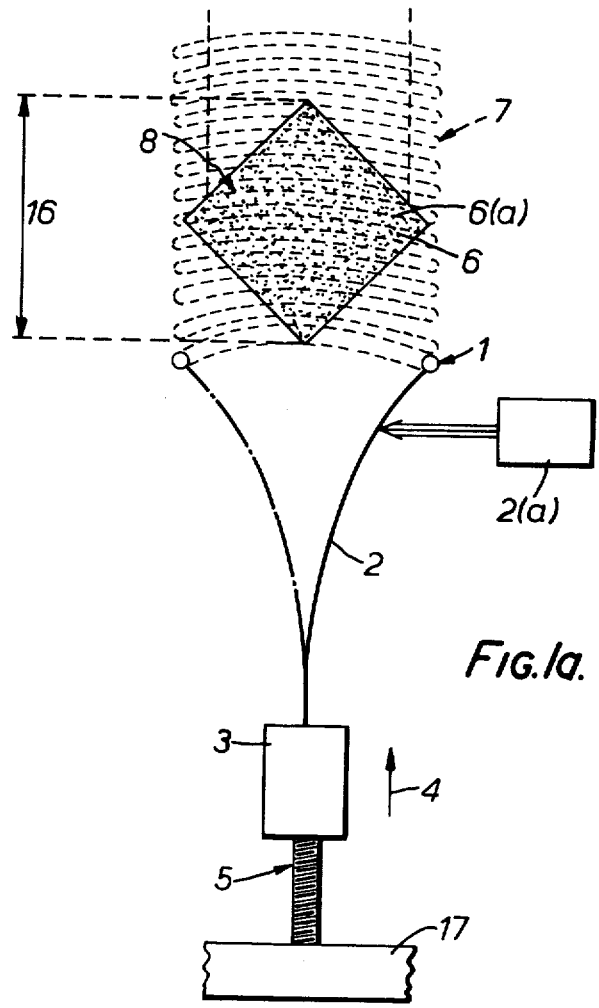
FIG. 1(a) illustrates schematically an embodiment of the present invention.
Figure 1C:
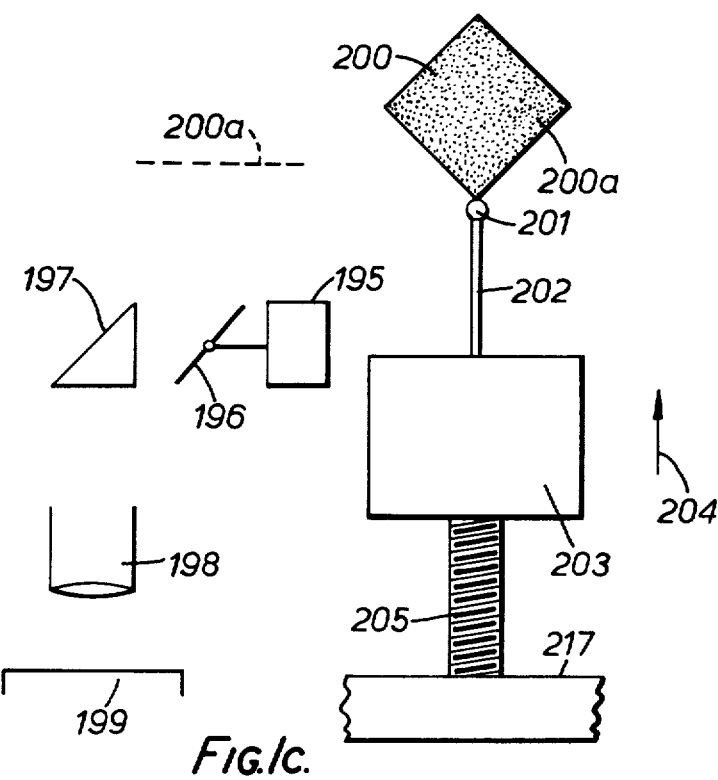
Figure 2:
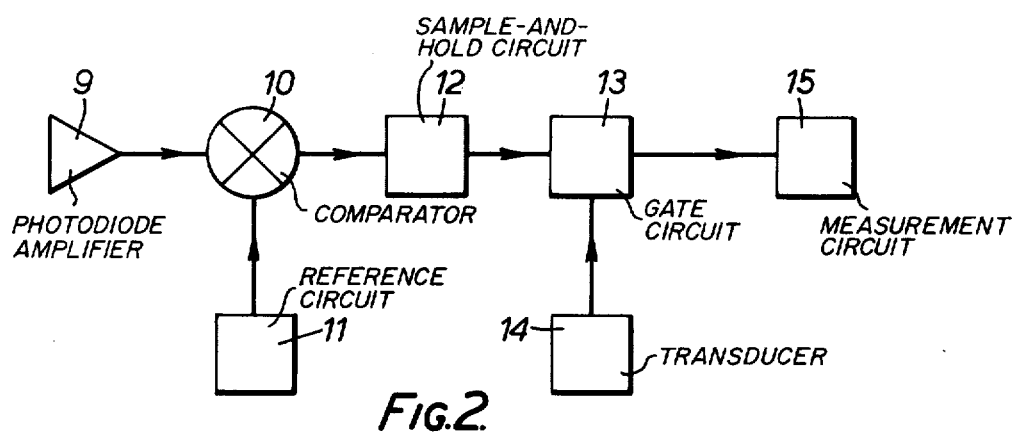
Figure 3A:
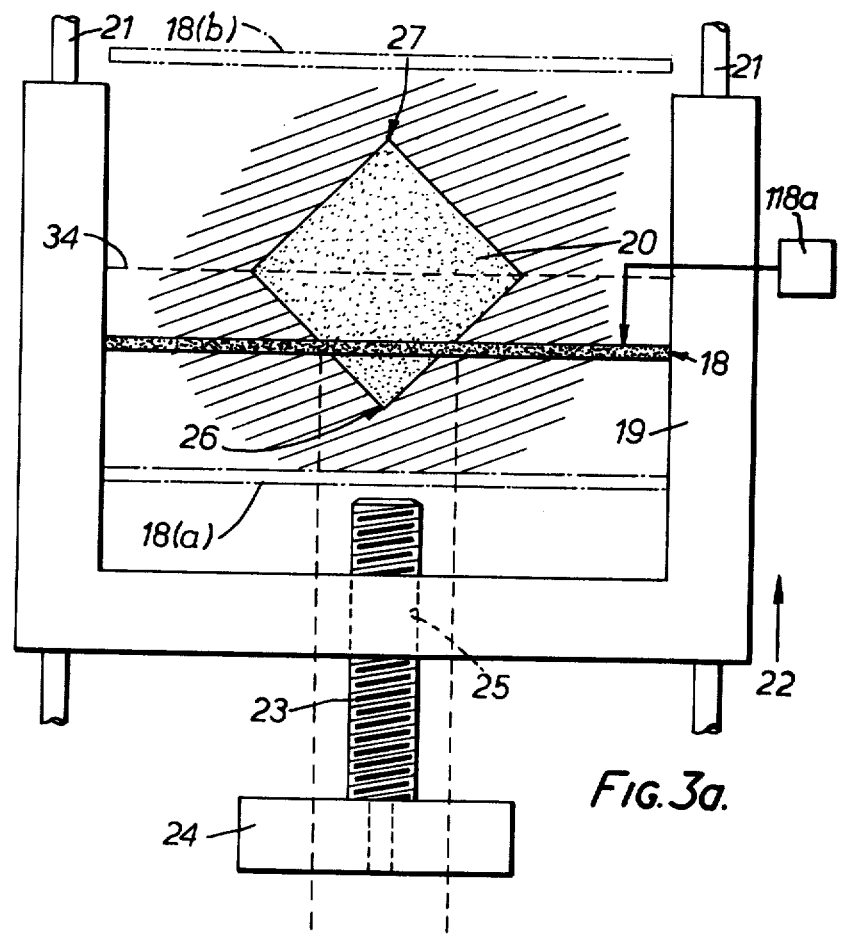
Figure 3B:
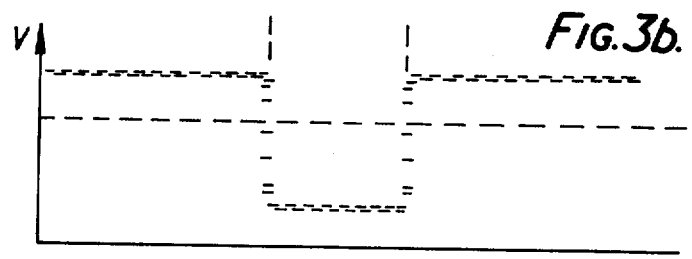
Figure 4A:
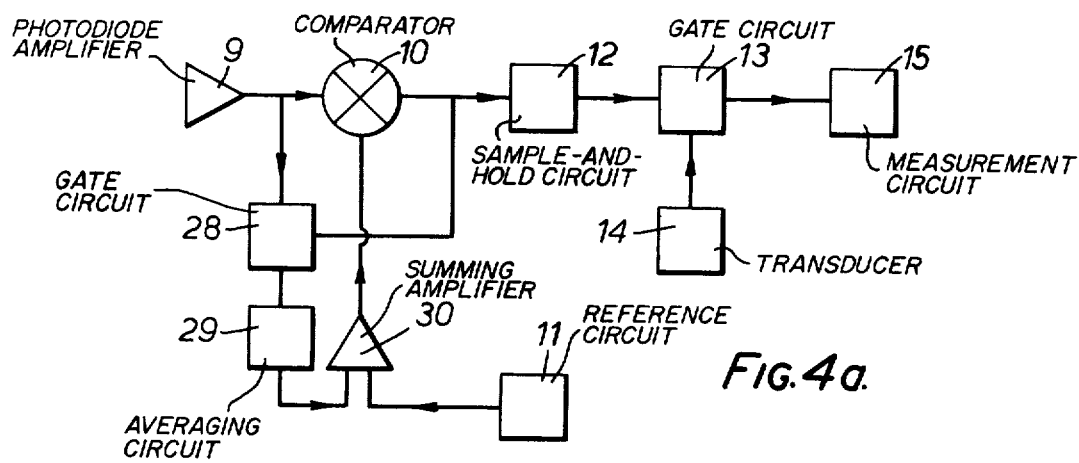
Figure 4B:
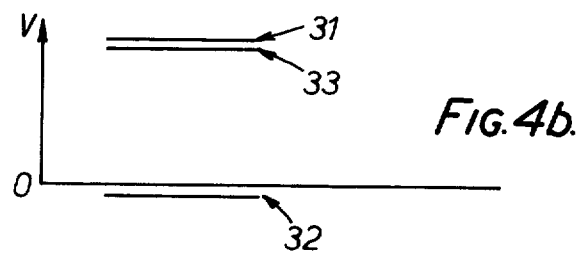
Figure 5A:
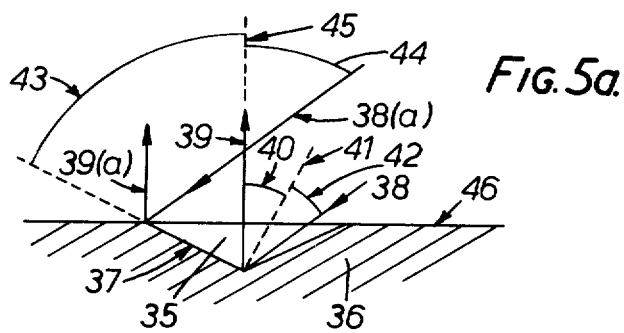
Figures 5B, 5C:
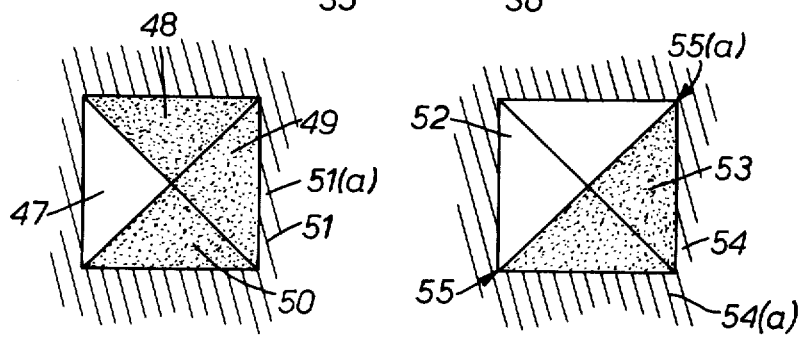
Figure 6A:
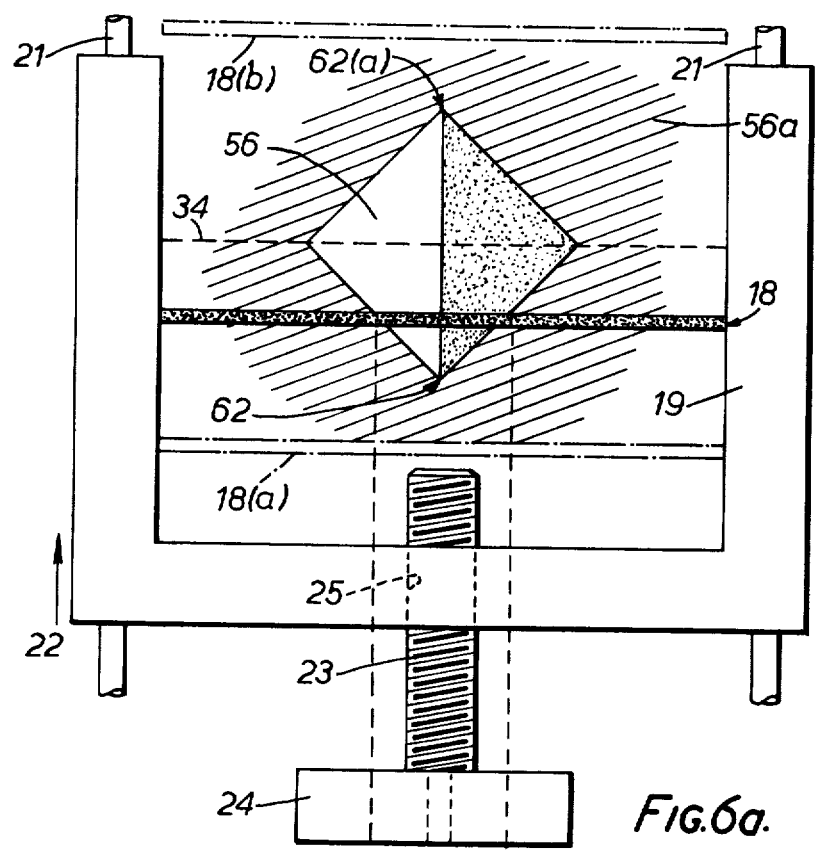
Figure 6B:
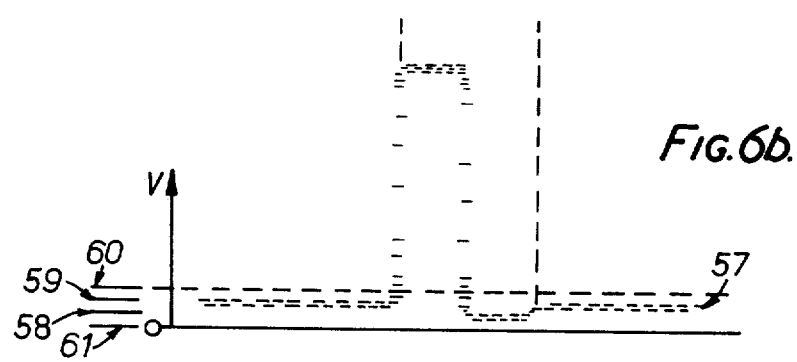
Figure 7:
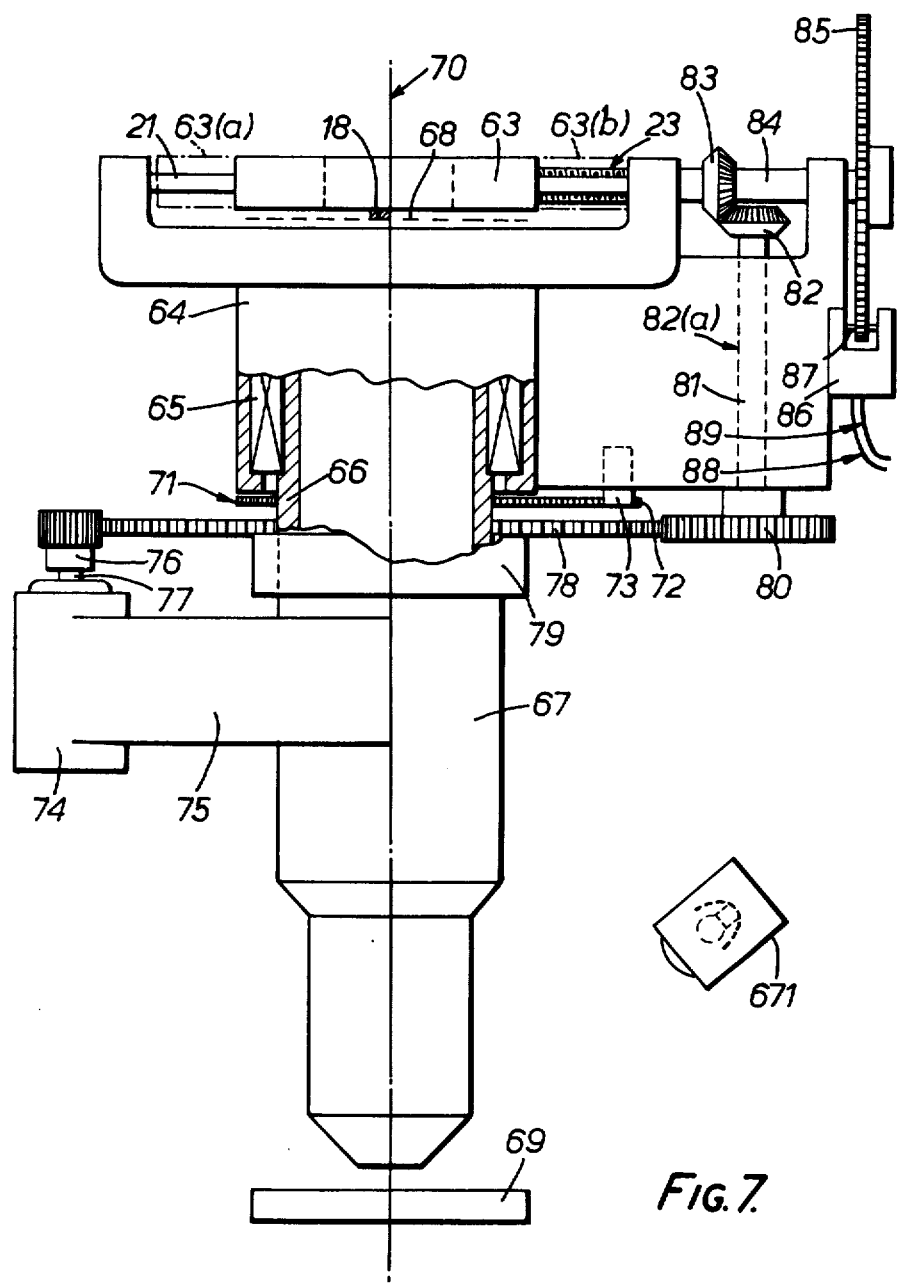
Figure 8A:
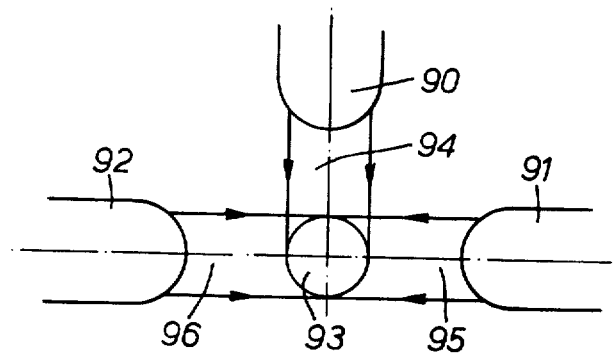
Figure 8B:
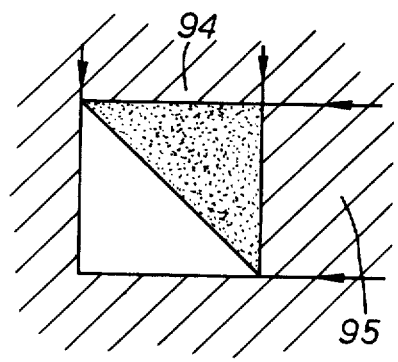
Figure 8C:
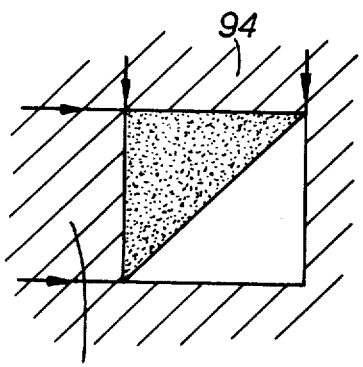
Figure 9:
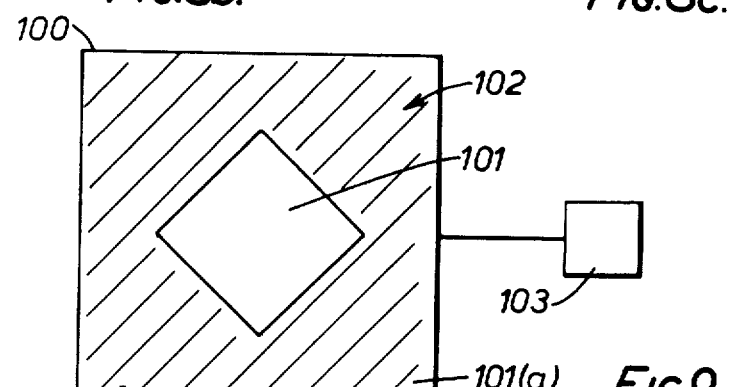

FIG. 1(c) illustrates schematically a modified form of the embodiment of the present invention shown in FIG. 1(a), FIG. 2 is a block circuit diagram, FIG. 3(a) illustrates schematically another embodiment of the present invention, FIG. 3(b) is a waveform diagram, FIG. (4a) is a block circuit diagram, FIG. 4(b) is a graph, FIGS. 5(a), 5,(b) and 5(c) are schematic diagrams illustrating modes of illumination of a surface to be investigated by means of an embodiment of the present invention, FIG. (6a) illustrates schematically a further embodiment of the present invention, FIG. 6(b) is a waveform diagram, FIG. 7 is a more detailed schematic diagram, comprising a partly cut-away side view, of an embodiment of the present invention, FIGS. 8(a), 8(b) and 8(c) are schematic diagrams illustrating modes of illumination of a surface to be investigated by means of an embodiment of the present invention, and FIG. 9 illustrates schematically parts of another embodiment of the present invention.

In one form of apparatus embodying the present invention, illustrated schematically in FIG. 1(a), photosensitive detection means are employed which comprise a single photodiode 1, and scanning means are used to cause relative scanning motion between photodiode 1 and the image in the image plane of a microscope of the apparatus. The photodiode 1 is oscillated mechanically in the image plane of the microscope (not shown), by means of which an indentation on a surface to be investigated is viewed, using in the scanning means for example a vibrating reed 2, driven to vibrate by mechanical or electromagnetic means indicated schematically at 2a, for instance by plucking, and the amplitude of the oscillation is selected so as to be sufficiently large to cover the largest image likely to be encountered. Imaging means of the apparatus provide for illumination of the indentation and the formation of an image of the region of the surface to be investigated in which the indentation is formed, in the image plane. In this case the imaging means comprise a microscope (not shown). The reed 2 is mounted on a traversable reed mounting 3 and as the reed 2, and hence photodiode 1, oscillates the reed mounting 3 is traversed in the direction of arrow 4 (transversely of the direction of oscillation of photodiode 1), using for example a screw 5, which may be driven by a motor (not shown). The rate of oscillation of reed 2 and the rate of traverse of reed mounting 3 are chosen so that the distance traversed in the direction of arrow 4 during one cycle of oscillation of reed 2 corresponds to the measurement resolution required. The photodiode is thus caused to scan an image 6 of an indentation formed in image plane 6(a) along a path shown by dotted line 7. The output of an amplifier circuit (not shown) electrically connected to the photodiode 1 provides electrical detection signals which vary in dependence upon the position of the photodiode with respect to the image 6 of the indentation. During a typical half-cycle of oscillation 8 the electrical detection signals generally vary as indicated in the graph of FIG. 1(b). It can be seen that the electrical detection signals change between levels indicating that the photodiode is within the image 6 of the indentation and that it is outside the image 6 of the indentation. It may be readily appreciated that for those oscillations of the photodiode 1 which do not cross the image of the indentation, no change in photodiode amplifier electrical detection signal level occurs. This difference forms the basis of the detection technique employed in this embodiment of the present invention, and may be used to activate a suitable measurement device attached to the traversing mechanism of the apparatus.

The block circuit diagram of FIG. 2 gives an example of how such changes in electrical detection signals can be utilised. The electrical detection signal output of a photodiode amplifier circuit 9 is fed into discrimination circuitry comprising a comparator circuit 10, where it is compared with a predetermined fixed electrical threshold signal derived from a reference circuit 11. This fixed electrical threshold signal has a magnitude approximately midway between the upper and lower levels (see FIG. 1(b)) of the electrical output of the photodiode amplifier circuit 9, and the output of the comparator circuit 10 provides discrimination signals which are either positive or negative electrical signals depending upon whether the photodiode 1 (FIG. 1(a)) is located inside or outside the image of the indentation (FIG. 1(a)). For assessing dimensions of the indentation the discrimination signals are passed to correlation means which comprise a sample-and-hold circuit 12 which responds only to positive (relatively high level) discrimination signals from comparator circuit 10 and gives an electrical output which is sustained for a time interval corresponding to one half-period of oscillation of the reed 2 (FIG. 1(a)) after a last positive discrimination signal from the comparator. Thus, as the photodiode 1 (FIG. 1(a)) oscillates across the image 6 of the indentation (FIG. 1(a)) the electrical output of the sample-and-hold circuit 12 is maintained constant and relatively high, but when the traverse in the direction of arrow 4 (FIG. 1(a)) carries the photodiode just past the image 6 of the indentation, the electrical output from the sample-and-hold circuit 12 diminishes within one half-period of oscillation of the reed 2 (FIG. 1(a)). This electrical output may then be used to activate a gating circuit 13, which admits electrical measurement signals from a transducer 14 to a compatible measurement circuit 15 only while the electricall output of the sampleand-hold circuit 12 is maintained constant and relatively high. Thus the measurement circuit 15 only measures the signals from transducer 14 while the photodiode 1 (FIG. 1(a)) crosses the image 6 of the indentation (FIG. 1(a)) during each half-cycle of oscillation of reed 2 (FIG. 1(a)).

The transducer 14 may be a device mounted on a fixed support member 17 and linked to the traversing screw 5 (FIG. 1(a)) in order to produce a train of electrical pulses or measurement signals directly related to rotation of this screw relative to the fixed support 17. Such a device, commonly known as a digitiser, can be linked through the gating circuit 13 to the measurement circuit 15, which in this case may be an electronic counter designed to count the pulses generated by the digitiser due to rotation of the screw 5. Operation of the gating circuit in response to the photodiode output in the manner described above ensures that pulses are only counted while the oscillating photodiode 1 is traversed across the enlarged image 6 of the indentation in the direction indicated by arrow 4. The number of pulses counted in one such traverse is thus a measure of the diagonal length 16 of the indentation. Thus, the positive and negative discrimination signals are correlated in relation to respective image areas, within and without the image 6 of the indentation, to provide on assessment of dimensions of the indentation.

Alternatively, the transducer 14 may be a linear variable differential transformer (LVDT) forming part of an a.c. circuit and linked directly to the reed mounting 3 and to the fixed support member 17. The electrical output of the a.c. circuit associated with the LVDT may be calibrated directly in terms of position of the reed mounting 3 in the direction of the arrow 4, relative to the fixed support 17, and the measurement circuit 15 may be designed to yield the diagonal length 16 in terms of the difference between the initial position signal, when the photodiode 1 first detects a corner of the image 6 of the indentation, and the final position signal, when the photodiode 1 no longer detects the image 6 of the indentation, having traversed across the full extent of a diagonal of the image 6 of indentation in the direction of arrow 4.

Alternatively, the transducer 14 may be an optical linear displacement device employing diffraction gratings to generate Moire fringes, with opto-electronic means of detecting displacement of these fringes. Such a device linked to the reed mounting 3 and to the fixed support member 17 will generate a train of electrical pulses (measurement signals) directly related to displacement of the reed mounting 3 relative to the fixed support 17 in the direction of arrow 4. Linking the electrical output of this form of transducer through the gating circuit 13 to the measurement circuit 14, which may be an electronic pulse counter, enables the diagonal length 16 to be determined in terms of the number of pulses counted during a traverse in the direction of arrow 4, in the manner described above for the digitiser.

The forms of transducer mentioned above are well known and are given by way of illustration only. Other forms of displacement measurement may be used provided they give adequate sensitivity and linearity, and are capable of yielding an electrical signal, directly or indirectly, suitable for transmission through the gating circuit 13 to the measurement circuit. It will be appreciated that the design of the gating circuit 13 and measurement circuit 15 may also be varied to suit the form of electrical signal transmitted by any particular type of displacement transducer.

The apparatus of FIG. 1(a) is described for completeness, but it is not the presently preferred form for this particular application in view of the readily appreciated need to arrange suitable means for oscillating the reed 2 at an appropriate frequency while maintaining the photodiode 1 accurately in the image plane. Although several such methods are available, such as plucking the reed 2 and allowing it to oscillate at its natural frequency, or driving the reed 2 at a chosen frequency by mechanical or electromagnetic means, an alternative approach is offered by the availability of various types of multiple photodiode arrays. These arrays allow many photodiodes to be disposed in the image plane of the microscope along a line orthogonal to the diagonal to be measured. A possible variation of the single photodiode apparatus of FIG. 1(a) should, however, be mentioned. In this variation a single photodiode is mounted on a rigid traversable mounting in place of the vibrating reed 2 and opto-mechanical means are provided to oscillate the image of the indentation across the photodiode in a direction orthogonal to the direction of traverse shown by arrow 4 in FIG. 1(a). An oscillating mirror may be used for this purpose, provided its motion is well-defined as in the case with mirror galvanometers commonly used in U-V recording instruments.

FIG. 1(c) illustrates schematically such a variation of the single photodiode apparatus of FIG. 1(a). In FIG. 1(c) a single photodiode 201 is mounted at one end of a rigid member 202 attached at its other end to a mounting 203 which can be traversed in the direction of arrow 204 using for example a screw 205 which may be driven by a motor (not shown). 217 is a fixed support member for screw 205.

The photodiode 201 travels in an image plane of the apparatus, schematically indicated as holding an image 200 of an indentation, at 200a in the Figure.

The image in the image plane is oscillated, for example by means as illustrated in the Figure at 195 to 199.

A region of the surface of a specimen 199, in which an indentation to be investigated is formed, is imaged by means of a microscope objective 198, a prism 197 and a mirror 196 in the image plane 200a. The mirror 196 is pivoted for oscillation and drive means 195 are provided for causing the mirror 196 to oscillate. Thus an oscillating image is formed in the image plane 200a.

An arrangement employing photosensitive detection means with a multiple photodiode array is shown in FIG. 3(a), in which a linear (one-dimensional) array 18 is mounted on an array mounting or carriage 19 so that the photodiodes in the array lie in the plane of an enlarged image 20 of an indentation. The linear array 18 is chosen so that its length is comparable to the dimensions of the image 20 of the largest indentation likely to be encountered, and the spacing between adjacent photodiodes in the array is chosen to be substantially constant and comparable to the resolution required in the measurement of diagonal length of the image 20.

Such an array 18 may typically consist of 256 photodiodes spaced along a line at intervals of 0.001 in., although other types of array are known comprising up to 1024 photodiodes at intervals of 0.0005 in. Such arrays generally consist of a single silicon chip treated photomechanically to form a row of photodiodes, and the same manufacturing processes are used to produce additional circuitry on the same chip. One such array, specifically the 256M manufactured by Integrated Photomatrix Ltd., incorporates scanning circuitry enabling the state of illumination of each photodiode to be examined in sequence, in response to a series of electronic address pulses (addressing signals) generated in a separate circuit mounted remotely from the array and connected to it by wires. The level of illumination experienced by a given photodiode gives rise to a corresponding value of electrical conductance across the photodiode, and this results in a leakage of electrical charge from a circuit associated with the photodiode and contained in the same silicon chip. When any photodiode is addressed by the electronic pulses generated by the separate remotely-mounted circuit, the leakage of electrical charge through the photodiode due to illumination gives rise to a decaying voltage level across the photodiode, and to an increase in the electrical charge input needed to restore this voltage to a predetermined level. Either of these parameters may be monitored to assess the level of illumination experienced by the particular photodiode, and the array then gives a corresponding signal output of short duration. This process takes place in sequence for all the photodiodes in the array one after another in turn, and the array output therefore consists of a succession of short pulses representative of the illumination level experienced by each individual diode in the array. The time taken to scan the array in this fashion may be varied by changing the frequency of the address pulses generated in the separate remote circuit, but may be typically 10 ms. Scanning circuitry for the array 18 is schematically illustrated at 118a in FIG. 3(a).

It will be appreciated that the serial signal output during one scan of the array 18 is a piece-wise analogy to the continuous signal obtained from the single photodiode 1 in FIG. 1(a) during one half-cycle of oscillation of the reed 2, and when the output of array 18 is amplified by suitable electronic means well known in the art, the resulting amplifier output electrical detection signals are of the form shown in FIG. 3(b). These electrical detection signals may be used in discrimination circuitry and correlation means in the manner already indicated in FIG. 2, except that amplifier 9 is now of a form compatible with the output signal of array 18, and the sample-and-hold circuit 12 of the correlation means is designed to sustain any positive signal from the comparator circuit 10 for the duration of one electronic scan of all the photodiodes in array 18. The gating circuit 13 may then be used to admit measurement signals from transducer 14 to the measurement circuit 15 as already described.

In the apparatus of FIG. 3(a), the carriage 19 forms part of scanning means of the apparatus and linear displacement of the carriage 19 along the fixed guides 21 causes the photodiode array 18 to be traversed across the enlarged image 20 of the indentation formed in image plane 20(a), in the direction of arrow 22. This displacement may be effected by means of a leadscrew 23 rotatably mounted in a fixed support 24 and cooperating with a threaded hole 25 in carriage 19. The leadscrew 23 may be driven by a motor (not shown) or other suitable means so as to urge the carriage 19 and array 18 in the direction of arrow 22 at a rate dependent upon the measurement resolution required in the detection of opposite corners 26, 27 of the image 20 of the indentation, and the rate of electronic scanning of the photodiodes in the array 18. If, for example, a measurement resolution of 0.001 in. is required, then it is necessary that the array 18 be advanced in the direction of arrow 22 by 0.001 in. in the time period required for one complete electronic scan of all photodiodes in the array 18. If this period is 10 ms, then the rate of displacement of carriage 19 and array 18 relative to the image 20 of the indentation in the direction of arrow 22 must be 0.1 in./s, and the rate of rotation and pitch of the leadscrew 23 must be chosen accordingly. Other means of displacing carriage 19 and array 18 may be employed, provided they meet this criterion.

Measurement of displacement may be effected by any of the means already outlined in the description of FIG. 2. As applied to the apparatus of FIG. 3(a), a suitable transducer (not shown) could be incorporated to give electrical measurement signals corresponding to displacement or position of the carriage 19 in the direction of arrow 22 with respect to the fixed support 24. Alternatively, a transducer may be used which gives electrical measurement signals corresponding to rotation of the leadscrew 23 with respect to the fixed support 24. In opration the transducer 14 (FIG. 2) would produce electrical measurement signals with a well-defined relationship to linear displacement of the array 18. At the beginning of its travel, the array at position 18(a) (shown in broken lines) would not coincide with any part of the image 20 of the indentation, and its serial output signal would be substantially constant and above the reference threshold level set into the reference circuit 11 of FIG. 2. In this condition, signals from the transducer 14 would not be accepted into the measurement circuit 15 of FIG. 2. In the course of its travel in the direction of arrow 22, however, the array 18 would encounter the corner 26 of the image, and one or more photodiodes would be less brightly illuminated than the rest, and the output signal(s) from these photodiodes would consequently fall below the general level, and below the reference level set into the reference circuit 11 of FIG. 2. In this condition, measurement signals from the transducer 14 would be accepted into the measurement circuit 15 of FIG. 2 and operation of the sample-and-hold circuit 12 would ensure that these signals would continue to be accepted for the period of one complete electronic scan of the photodiodes in the array 19 after the last of the output signals below the general level is received at comparator 10, (i.e. after the last discrimination signal which is positive or relatively high level) by which time photodiodes towards the centre of the array would again give signals below the reference level, thus ensuring that measurement signals from the transducer 14 would continue to be accepted into the measurement circuit 15 of FIG. 2. This process would be repeated, the array elements being scanned in cyclically repeated sequence, giving continuous acceptance of transducer signals into the measurement circuit of FIG. 2 until the array 18 had traversed the full extent of the image 20 in the direction of arrow 22. Thus during one complete traverse of the array 18 from position 18(a) to 18(b), transducer signals would be accepted into the measurement circuit corresponding to the length of the diagonal of the image 20 of the indentation.

In an alternative embodiment, in which the need to provide a transducer 14 is avoided, pulses used to address a photodiode of the array are fed as measurement signals to measurement circuit 15 in place of the signals from the transducer. For example pulses used to address the first photodiode of the array, in respective scans of the array, may be used.

It will be readily appreciated that the reference threshold voltage generated in the reference circuit 11 of FIG. 2 must lie between the voltages resulting from amplification of array signals corresponding to photodiodes subjected to high and low levels of illumination in the image plane, the high levels representing illumination of the surface of the hardness specimen surrounding the indentation, and the low levels representing the indentation itself. It would, in principle, be desirable to set the reference voltage generated in the reference circuit 11 of FIG. 2 as close as possible to the higher voltage resulting from illumination of the specimen surface surrounding the indentation, in order to admit measurement signals from the transducer 14 to the measurement circuit 15 as soon as possible after any photodiode in the array of FIG. 3 has received a lower level of illumination upon entering the image of the indentation. In this way the sensitivity of detection of the image may be increased, resulting in a more accurate measurement of the diagonal length. Difficulties are encountered, however, when using the reference circuit 11 of FIG. 2 in this way, since the higher voltage resulting from illumination of the specimen surface surrounding the indentation is not fixed, but varies from specimen to specimen in an indeterminate fashion. Thus, with a fixed reference voltage, the sensitivity of detection of the image is likely to vary from one specimen to another, and measurement accuracy is likely to be inconsistent.

One technique which may be used to overcome this difficulty is embodied in the modified measurement circuit of FIG. 4(a). The incoming signal from the array is amplified in the input amplifier circuit 9 and the resulting electrical detection signals supplied to the discrimination circuitry comprising a comparator circuit 10 and a gating circuit 28 connected parallel with one another. This gating circuit is switched on in the absence of a positive discrimination signal from the output of the comparator circuit 10, and then allows electrical detection signals from the amplifier circuit 9 to enter an averaging circuit 29. The average voltage output from circuit 29 is supplied to a summing amplifier 30, where it is added to the reference voltage from the reference circuit 11, and the sum of these two voltages is supplied to the comparator circuit 10 as a threshold voltage therefor. The comparator circuit 10 thus receives a steady electrical signal corresponding to the average photodiode output resulting from general illumination of the surface of the particular specimen being assessed, together with the reference voltage from the reference circuit 11, the latter voltage being adjustable to within fine limits and in the opposite sense to the output of the averaging circuit 29. This is illustrated in the graph of FIG. 4(b), where voltage levels corresponding to the outputs of averaging circuit 29, reference circuit 11 and summing amplifier 30 are shown as lines 31, 32 and 33 respectively. In operation, while successive signals from photodiodes in the array, as amplified by input amplifier 9, exceed the voltage level 33, there is a negative output from comparator 10, and the gating circuit 28 allows input signals into the averaging circuit 29, thus maintaining an up-to-date value for the signal 31 corresponding to general illumination of the specimen surface. When any given photodiode in the array is subjected to a lower illumination level, the output from amplifier 9 falls below the level indicated by line 33 and a positive output signal is produced from comparator 10. This output causes the gating circuit 28 to inhibit the input of photodiode signals into the averaging circuit 29, thereby preventing the general illumination signal 31 from falling; this signal is maintained substantially constant in the absence of input signals into the averaging circuit 29. The positive output signal from comparator 10 also activates sample-and-hold circuit 12 and thence gating circuit 13 to admit signals from transducer 14 into measurement circuit 15, as already described.

Although the above description refers to positive and negative voltage levels for specific signals, polarities may be changed to suit particular electronic design requirements, provided the functional arrangement is unchanged. Thus for exaple, the two inputs to summing amplifier 30 may be via one inverting and one non-inverting terminal, in which case the signals from averaging circuit 29 and reference circuit 11 may be of the same polarity, rather than of opposite polarity as described above.

Another major consideration in the use of the foregoing arrangements for measuring the diagonal length of a pyramidal indentation is the need to reject all surface features other than the indentation in question. This may not always be readily directly achievable with the systems so far described, because they are designed to detect contrast in the enlarged image of the specimen surface, and with the method of illumination normally used for Vickers hardness measurement, other surface features such as grinding marks and porosity can give rise to areas of contrast in the image similar to that corresponding to the indentation itself.

Methods proposed for dealing with this situation consist in identifying some property of the indentation which is not shared by other surface features likely to be in the field of view of the microscope. The obvious characteristic of the hardness indentation is its geometry, resulting from the impression of a square-base diamond pyramid of 68° semi-angle into the specimen surface, and it is possible to envisage adapting the discrimination circuitry, the correlation means and the measurement circuits outlined above to reject those measurements which do not conform to the expected geometrical pattern. In the arrangement of FIG. 3(a), for example, the frequency of scanning photodiodes in the array 18, and the speed of traversal in the direction of arrow 22 may be chosen so that, on each scan of the array 19, an integral number, say 2, more photodiodes are likely to detect the image 20 of the indentation than on each preceding scan; once past the centre line 34 of the image 20 the situation is reversed, and 2 fewer photodiodes are likely to detect the image 20 than on each preceding scan. This requirement may be met by incorporating an up/down counter (not shown) in the circuit of FIG. 4(a), which in the presence of a positive signal from comparator 10 would count the photodiode address pulses generated in the separate remote circuit (not shown) supplying the array. A limit circuit (not shown) would receive signals from the up/down counter corresponding to the number of photodiodes detecting the indentation on each scan of the array, and this circuit would be arranged to inhibit and reset the measurement circuit 15 (FIG. 4) if the absolute value of the change in the number of photodiodes counted on successive electronic scans of the array differed significantly from the expected increment. Thus, if the expected increment were 2, the limit circuit could be arranged to inhibit and reset the measurement circuit 15 for actual increments outside the range 1 to 3, thereby allowing for minor deviations from the ideal geometry of the image while avoiding spurious measurements due to the presence of other surface features in the field of view.

Although technically feasible, this approach could suffer from failure to produce any measurement on samples which have a significant number of surface features in addition to the diamond indentation, since the measurement will be inhibited if at any stage during its traversal across the image of the indentation the array encounters the image of another surface feature. This may be catered for by the use of additional digital electronic circuitry to further analyse the signals from the photodiode array and thereby discriminate in favour of the indentation geometry, but this can lead to significant extra complication in the electronic signal processing circuitry in order to incorporate further criteria for acceptance of the diagonal measurement.

A simpler approach is used in a presently preferred form of the present invention, involving the use of a imaging means providing different method of illumination from the vertical illumination described above in order to highlight particular facets of the indentation and thereby produced improved contrast in the image, while reducing contrast in the images of any other surface features. A method employed relies upon the fact that indentations made by multifacetted indenters of predetermined form (e.g. pyramidal diamond indenters) in homogeneous ductile materials closely match the indenter geometry and possess four essentially flat facets which act as good specular reflectors of light. Furthermore, in the Vickers Hardness test the semi-angle (68°) of an indentation formed by the square-based pyramidal indenter used is sufficiently large to permit a parallel beam of light incident upon any given facet at an appropriate angle to be reflected specularly from the entire surface of that facet in a direction normal to the nominal surface of the hardness specimen. This technique is illustrated in FIG. 5(a) in which an identation 35 is shown contained in a right sectional view of a specimen 36 and one of the facets 37 of indentation 35 is illuminated by a parallel beam of light 38, 38(a). The good specular reflecting properties of facet 37 result in the major proportion of the reflected light being transmitted as a parallel beam 39, 39(a) at an angle 40 with respect to the normal 41 to the facet 37 such that angle 40 is equal to the angle of incidence 42 of the light beam 38, 38(a). Furthermore, because the semi-angle 43 of the indentation 35 is greater than twice its complementary angle (i.e. exceeds 60°), angle 44 of the input beam 38, 38(a) relative to normal 45 to surface 46 of specimen 36 may be chosen so that the reflected beam 39, 39(a) lies along the normal 45. With a semi-angle 43 of 68°, the angle 44 of the input beam 38, 38(a) relative to normal 45 is thus 44°. It will be appreciated that a microscope (not shown) forming part of imaging means of hardness testing apparatus, or other suitable optical system arranged to view the indentation, having its optical axis lying substantially along normal 45, will form an image of the indentation illuminated as described in which one facet will appear with greatly enhanced brightness compared with the other facets and the remainder of the specimen surface. Other surface features, such as machining marks or porosity, cannot give rise to bright images unless they possess significant areas with an orientation relative to the input light beam 38, 38(a) closely similar to that of the brightly illuminated facet 37. In the rare event where closely similar orientation existed, it is unlikely that the reflecting properties of such an area would match those of the facet 37, and the brightness of the image of such an area would be low compared with that of the facet 37 of the indentation 35. This has been verified in numerous tests, and it has been observed that this method of illumination, in conjunction with viewing along the line of specular reflection from a facet, gives rise to a particularly high brightness in the image of that facet, thus affording a means of discriminating against other surface features.

The image of the indentation 35 illuminated as in FIG. 5(a), produced by a microscope, or other suitable optical system forming part of imaging means of the apparatus, arranged with its optical axis substantially along normal 45, appears as shown in FIG. 5(a), with the illuminated facet 37 appearing as a bright triangle 47 and the other three facets appearing as relatively dark triangles 48, 49, 50. The image 51 of the surface 46, formed in image plane 51(a) surrounding the indentation 35 is generally slightly brighter than the images of the non-illuminated facets of the indentation due to diffuse reflection but the image brightness in this region is considerably less than within the bright triangle 47.

When the method of FIG. 5(a) is applied to the illumination of two adjacent facets, the image produced by a microscope or other suitable optical system arranged with its optical axis substantially along normal 45 appears as shown in FIG. 5(c), with the two illuminated facets appearing as a single bright triangle 52 and the two non-illuminated facets appearing as a relatively dark triangle 53. Image 54 of the specimen surface surrounding the indentation formed in image plane 54(a) is brighter than when only one facet is illuminated, but remains considerably less bright than the triangle 52. It will readily be appreciated that this method of illumination, giving an image as shown in FIG. 5(c), is particularly appropriate for automatic diagonal measurement in the Vickers hardness test, since a line 55 to 55(a) at the junction of the bright triangle 52 and the dark triangle 53 represents the diagonal of the indentation, and the brightness of triangle 52 renders this particularly easy to detect by opto-electronic means, while retaining the inherent advantages of this method of illumination in discriminating against other surface features.

A further consideration also renders the use of a mode of illumination as explained with reference to FIGS. 5(a) to 5(c) desirable in embodiments of the present invention. The individual photodiodes of the array 18 of FIG. 3(a), for example, are, it will be appreciated, of a small size, in order to obtain the desired resolution over an image of an indentation formed in the image plane where the array 18 is located. The small size of the photodiodes may mean that their response to changes in light level is relatively slow. If this is the case, it may be necessary, in order that measurements of dimensions of an indentation can be carried out at a conveniently rapid rate, to ensure that a suitably bright image is presented for examination by the array 18. The method of illumination explained with reference to FIGS. 5(a) to 5(c) involving specular reflection from facets of an indentation, can readily provide such a suitably bright image.

FIG. 6(a) shows the apparatus of FIG. 3(a) arranged to inspect an image 56 of an indentation illuminated as described above for FIG. 5(c). The amplified output signals (electrical detection signals) during one electronic scan of the photodiode array 18 in the plane 56(a) of image 56 is shown as 57 in FIG. 6(b), which illustrates the large response obtained from those photodiodes in the array which coincide with the image of the brightly illuminated facets of the indentation. This apparatus may be used with the electronic circuitry of FIG. 4(a) adjusted to detect array signals corresponding to increased image brightness rather than those corresponding to diminished image brightness, as described previously. The comparator 10 of the discrimination circuitry then gives a positive signal to initiate measurement of measurement signals from the transducer 14 only when the voltages of amplified photodiode signals from the input amplifier 9 exceed the voltage output of the summing amplifier 30, which in this case represents the positive sum of the output from the averaging circuit 29 and the reference circuit 11. The approximate relationships between these voltages may be as indicated in FIG. 6(b), where the reference circuit output is represented by the line 58, the averaging circuit output by the line 59, and the summing amplifier output by the line 60, all relative to OV shown as the line 61. It will be appreciated that any amplified photodiode signal (electrical detection signal) 57 which exceeds the summing amplifier output 60 then initiates the measurement process; this condition exists throughout the traversal of array 18 across the image 56 of the indentation in the direction of arrow 22 (FIG. 6(a)), and provided that image 56 is orientated with its diagonal 62, 62(a) parallel to arrow 22, measurement of the length of the image diagonal 62, 62(a) may be accomplished by arranging the transducer 14 of the measurement circuit of FIG. 4(a) to give signals corresponding to the said traversal of the array. (Various types of transducer 14 and means of using them in this application have been briefly covered in the description of FIG. 2).

In its standard form, the Vickers hardness test calls for measurement of the lengths of both diagonals of the indentation made by the pyramidal diamond indenter. The arrangement of FIG. 6(a), used in conjunction with the method of illumination of FIG. 5(c) and with the electronic circuitry of FIG. 4(a) in the manner described above, constitutes a presently preferred method of measuring a single diagonal length. As the diamond indenter is a square-based regular pyramid, the diagonals of the indentation are mutually perpendicular when viewed along the same axis relative to the specimen as that used when impressing the indenter into the specimen surface. Thus, provided the microscope or other suitable optical system of the imaging means is arranged to view the indentation in this way, the diagonals of the enlarged image of the indentation will be mutually perpendicular. In practice, with an indenter impressed vertically down into the specimen surface, it is necessary only to arrange to view the indentation vertically for this criterion to be met, provided the orientation of the specimen is unchanged. The apparatus of FIG. 6(a) may then be arranged to permit measurement of both diagonal lengths in the image of the indentation by means of a suitable mounting allowing rotation through the right-angle about an axis perpendicular to and passing through the centre of the image plane, while maintaining the array 18 in the image plane. This may be effected for example, by means shown in FIG. 7, in which a traversing assembly (traversable array mounting) 63 similar to the arrangement shown in FIG. 6(a) is mounted on guides 21 in a housing 64, in which a combined radial and thrust bearing 65 serves to locate the entire assembly on the tube 66 of a microscope 67 or other suitable optical system providing an enlarged image 68 of an indentation (not shown) formed in the surface of a specimen 69.

The microscope or other suitable optical system forms part of the image means of the apparatus. The other part of the imaging means provides for the illumination of the specimen 69. The illumination may be provided by electrical light sources or mirrors for example, as schematically indicated at 671 in FIG. 7.

Bearing 65 permits the housing 64 to rotate about a central axis 70 of the microscope 67 while providing rigid location along axis 70 thus maintaining the photodiode array 18 in the plane of the image 68. The degree of rotation of housing 64 is restricted by a limit plate 71 which is rigidly fixed to the tube 66 and has two peripheral projections 72 which co-operate with a peg 73 rigidly mounted in housing 64 to limit the degree of rotation of the latter relative to the tube 66 to a full right-angle. The angular position of the limit plate 71 about the central axis 70 is adjusted so that at one limit of rotation of housing 64 the traversing assembly 63 may be urged along the guide 21 by the leadscrew 23 in a direction parallel to one diagonal of the enlarged image 68 of the indentation, and at the other limit of rotation of housing 64 the movement of the traversing assembly 63 is in a direction parallel to the other diagonal of the image 68.

Another feature of apparatus of FIG. 7 is the method adopted for driving the rotational and traversing motions, both of which are provided by a single constant speed reversing electric motor 74 rigidly attached to the microscope 67 by means of a bracket 75. The motor 74, which may be a low speed machine or an assembly combining a higher speed motor with suitable reduction gearing, is provided with a gear pinion 76 fixed to its output shaft 77. Pinion 76 co-operates with a larger diameter gear wheel 78 which is free to rotate on a radial bearing 79 about the axis 70 of the microscope tube 66 but is maintained in a fixed axial position along the tube 66 by a suitable thrust bearing (not shown). Another pinion 80 is fixed to one end of a shaft 81 passing through and free to rotate in housing 64 and supported in a sleeve bearing 82(a). Pinion 80 co-operates with gear wheel 78 and serves to transmit rotational motion to a bevel gear 82 fixed to the other end of shaft 81 and co-operating with another bevel gear 83 fixed to a shaft 84 one end of which is formed into the leadscrew 23. The design of the arrangement is such that appreciably greater torque must be supplied to gear wheel 78 in order to overcome the rotational friction associated with pinion 80, shaft 81, bearing 82(a) bevel gears 82, 83, shaft 84 in its bearings (not shown) in the housing 64, and the leadscrew 23 co-operating with the threaded portion (not shown) of the traversing assembly 63, than is required to overcome the friction associated with rotation of housing 64 about the microscope tube 66 on bearing 65. Consequently, when electrical power is supplied to the motor 74 causing pinion 76 to rotate and thereby driving gear wheel 78, the initial effect is to rotate housing 64 and the components supported thereby about the axis 70 until the peg 73 contacts one or other of the projections 72, thus preventing further movement. In this condition, the motor 74 draws additional electrical power and gives an increased torque output, which then overcomes the rotational friction associated with items 76, 78, 80, 81, 82, 82(a), 83 and 84, and causes the leadscrew 23 to rotate, thereby traversing the assembly 63 along the guides 21 and a direction parallel to one diagonal of the image 68.

When the traversing assembly 63 is at the limit of its travel 63(a) in one direction it contacts a microswitch (not shown) which actuates a relay (not shown) to change the direction of rotation of the motor 74. Because of the difference in rotational friction described above, the initial effect of this is to rotate housing 64 until the peg 73 contacts the other projection 72, thus preventing further movement.

The leadscrew 23 is then caused to rotate in the sense opposite to that of its previous rotation, thus causing assembly 63 to traverse along the guides 21 in a direction opposite to its previous motion and parallel to the other diagonal of the image 68. At the limit of its travel 63(b) in this direction the assembly 63 contacts a second microswitch (not shown) which restores the relay (not shown) to its original state, so restoring the original direction of rotation of the motor 74 and permitting the complete cycle to re-commence. In a practical embodiment it is convenient to arrange for interruption of the supply of electrical power to the motor 74 after both diagonals of the image 68 have been scanned. This may be initiated by one or other of the microswitches referred to above actuating a second relay (not shown) to interrupt the electrical supply to the motor 74 when the assembly 63 is at one end or the other of its traverse. An external switch (not shown) may then be used at will to restore the supply to motor 74 and thereby initiate a further complete cycle of movement as described. As an alternative to a system of microswitches and relays for controlling the motor 74, an electronic or opto-electronic switching system may be employed, provided essential functions as described are carried out.

The arrangement of FIG. 7 includes one possible design of transducer 14 (FIG. 4(a)) comprising a toothed wheel 85 fixed to an extension of shaft 84 and a light emitter/detector assembly 86, which incorporates a solid state light source and a light detector so arranged that the source is directed towards the detector. When connected to a suitable low-voltage electrical supply, a beam of light 87 emitted from the source increases the electrical conductance of the detector, and a current flows in the conducting leads 88, 89, the remote ends of which are connected to the low voltage supply (not shown). Such emitter/detector assemblies are well known and available commercially from a number of suppliers. When the light beam 87 is interrupted by an opaque object, the conductance of the detector decreases, and the current flowing in the leads 88, 89 is much reduced. The relative positions of toothed wheel 85 and the emitter/detector assembly 86, and the dimensions of the teeth on the periphery of toothed wheel 85, are so chosen as to produce regular periodic interruption of the light beam 87 when the shaft 84 is rotated at a constant rate. This has the effect of producing a regular periodic series of current pulses in the leads 88, 89 at a frequency directly related to the rate of rotation of the shaft 84, and hence to the rate of traverse of the assembly 63 carrying the photodiode array 18 across the image 68 of the indentation. This series of current pulses in leads 88, 89 may then be supplied to the gating circuit 13 of FIG. 4(a) for counting by a suitable measurement circuit 15 only when the image 68 of the indentation is detected, in the manner described previously, thus giving a measurement of the diagonal length of the image 68.

Any appropriate form of displacement transducer may be incorporated in the arrangement of FIG. 7, which in combination with a compatible measurement circuit 15 admits of alternative means of measuring the diagonal length of the image 68. The transducer design shown in FIG. 7 is however particularly appropriate in this application, since the production of a regular series of pulses for transmission to the measurement circuit 15 (FIG. 4(a)) allows digital electronic techniques to be used in circuit 15, and in subsequent circuitry designed to calculate and display the Vickers hardness number from the lengths of both diagonals expressed in terms of pulse counts. The standard expression for the calculation of Vickers hardness may then be modified to give $$HV = 2F \sin 68° \left(\frac{pm}{n}\right)^2$$

where
p is the fixed number of pulses per mm of travel of the traversing assembly 63,
m is the fixed linear magnification of the image 68, and
n is the average of the two pulse counts corresponding to both diagonal lengths in the image of an indentation.

Techniques well known in the field of digital electronic processing may be used to compute the Vickers hardness value from the lengths of both diagonals in the image 68 expressed in terms of pulse counts, given the fixed values of p and m and the load applied when making the indentation being measured. Possible arrangements include various forms of electronic computer suitably programmed, microprocessor systems adapted to this application, through to purpose-designed electronic calculator integrated circuits. The provision from such arrangements of a digital readout of hardness can provide for the use of automatic machines which automatically sort specimens in accordance with the hardness determined for them.

The arrangement of FIG. 7 may be used to assess indentations under any appropriate conditions of illumination, but the preferred method is that indicated in FIG. 5(c), applied to the simultaneous illumination of two adjacent facets of the indentation.

FIGS. 8(a), 8(b) and 8(c) show two possible arrangements by which the indentation may be illuminated in order to highlight the facets and thereby yield an image as depicted in FIG. 5(c). FIG. 8(a) shows a plan view of a system of three identical light sources 90, 91, 92 of imaging means of hardness testing apparatus positioned so as to illuminate three facets of an indentation located in a small area 93 in a surface 94 of a hardness specimen, the area 93 representing the field of view of the microscope 67 (not shown) in the arrangement of FIG. 7.

The three sources 90, 91, 92 are designed to give similar essentially parallel beams of illuminating light 94, 95, 96 respectively, which may be switched on in sequence to illuminate adjacent facets of the indentation as described previously.

This is illustrated in FIG. 8(b), which shows an enlarged view of the indentation as illuminated by the light beams 94 and 95. With illumination by beams 94 and 96, the indentation appears as depicted in FIG. 8(c). Any suitable means may be adopted to arrange switching of the light sources 90, 91 and 92, in phase with operation of the system shown in FIG. 7, thus enabling the measurement of both diagonals alternately. Suitable means include switching the supply of electrical power to the light sources 90, 91, 92, or alternatively the use of a system of movable shutters while keeping the light sources switched on, or alternatively the use of a suitable optical system incorporating one or more movable mirrors to direct the light beams as shown in FIGS. 8(*b*) and 8(*c*). In the case of designs employing movable shutters or movable mirrors, mechanical or electromechanical means of actuation may be employed to maintain the required phase relationship between the system of illumination and the measurement system of FIG. 7.

The various systems described so far relate to assessment of hardness as defined in various standards for the Vickers Hardness test, all based upon the standard expression given hereinabove. The standard expression relates hardness to the indenter load, divided by the square of the mean diagonal length, the latter term representing twice the superficial area of the hardness indentation, assuming that this area is square as intended. Denoting the superficial area by A, the hardness expression therefore becomes:

$$HV = \frac{F \sin 68°}{A}$$

which is an estimate of the average pressure applied to the facets at the completion of their formation by the indenter.

The standard expression is normally restricted in its application to those indentations where the edges are reasonably straight, in the interests of accuracy, but there is a possibility that the above-modified expression could be employed for the assessment of less regular indentations, such as those where the edges are curved due to the formation of a raised rim, provided a suitable method could be found for the precise estimation of the superficial area. This is relevant to the above description of the various systems for measuring diagonal lengths opto-electronically, since very similar arrangements can be envisaged for the measurement of superficial area. The system shown in FIG. 6(*a*), for example, could be adopted for this purpose if extra illumination were provided to highlight all 4 facets of the indentation simultaneously, using an extension of the method shown in FIGS. 5(*a*), 5(*b*) and 5(*c*). The image of the indentation in FIG. 6(*a*) would then be a square of substantially uniform brightness, and each electronic scan of the array 18 would yield enhanced signals from those photo-diodes lying in the plane of the bright image.

An adaptation of the measurement circuit of FIG. 4(*a*) may be used to process these signals, and for this purpose the sample-and-hold circuit 12 may be modified, and transducer 14 is not longer required. In place of transducer 14, signals (addressing signals) from the circuit (not shown) in scanning circuitry of the apparatus used to drive the photodiode array may be used. In this circuit a regular periodic pulsed electronic signal is generated, and the frequency of these so-called clock pulses directly determines the rate at which successive photodiodes in the array are addressed. The time interval between successive clock pulses (and hence addressing signals) is thus equal to the time interval between the array output signals corresponding to adjacent diodes, and the scan time of the total array is therefore determined by the product of this time interval and the number of diodes in the array. The leadscrew 23 of FIG. 6(*a*) may be driven by a constant-speed motor (not shown) or other means in order to ensure that the carriage 19 carrying the array 18 traverse the array across the image of the indentation at a fixed rate, in the direction of arrow 22. The rate of traverse may be chosen so that the distance travelled by array 18 during one complete electronic scan is equal to the dimensional resolution required for measurement of the image of the indentation.

Under these conditions, an enhanced signal from any particular photodiode during a given electronic scan of the array 18 may be considered to represent part of the bright image of the indentation with a substantially rectangular area, the size of which is given by the product of the dimensional resolution and the photodiode pitch in the array. This area, when multiplied by the total number of enhanced photodiode signals received during the mechanical traverse of the array over the enlarged image of the indentation, thus yields an estimate of the total superficial area of the indentation.

The measurement circuit of FIG. 4(*a*) may be used as previously described, with modification to the sample-and-hold circuit 12 to permit each discrimination signal from comparator 10 to be held for a period corresponding to the time interval between successive clock pulses generated in the circuit during the array (i.e. the period between the scanning of one element of the array and the next). A succession of enhanced photodiode signals results in a regular series of discrimination signals from comparator 10, thus giving rise to a continuous electronic signal from the sample-and-hold circuit 12, which is used to activate the gating circuit 13, thus channelling clock pulses or addressing signals, in place of signals from transducer 14, through to the counting or measurement circuit 15. The total number of pulses N counted during one complete mechanical traverse of the array across the image of the indentation corresponds to the total number of enhanced photodiode signals received, and may be used in the expression:

$$HV = \frac{F \sin 68° \, m^2}{Na}$$

where $Na/m^2 = A$, the superficial area of the indentation, m is the linear magnification of the image of the indentation, and a is the incremental area given by the product of the dimensional resolution and the photodiodes pitch in the array.

Means similar to those discussed previously may be used to calculate the hardness number HV from the above data, and HV may be displayed automatically in a numerical form.

This method can provide several advantages over the above method, described earlier, of which the ability to assess indentations with curved sides is readily apparent. Practical advantages also exist, because the measurement involves only one mechanical traverse, which avoids the need for a means of rotating the measurement assembly through 90°, and the orientation of the direction of traverse relative to the indentation is not critical. An additional benefit is that measurement is carried out in less than half the previous time.

Two-dimensional photodiode arrays, in which they are many parallel rows of photodiodes, may be used in place of linear arrays in the system described above. Mechanical arrangements for traversing are then unnecessary, information being obtained by electronically scanning all diodes in the first row, in sequence, then all diodes in the second row and so on until all photodiodes in the array have been sampled. The serial output signal from such an array may be used in two ways. If a diagonal measurement is required, the output may be fed into the circuit of FIG. 4(a), and electronic addressing signals generated in scanning circuitry external to the array and causing successive rows of photodiodes to be addressed may be supplied to the gating circuit 13, in place of signals from the transducer 14 previously described. The diagonal measurement will then accumulate in counter 15 in terms of the number of rows of photodiodes in which an enhanced signal is generated, due to the detection of part of the bright image of the indentation by one or more photodiodes in each row. The diagonal length is the product of the number of such rows and the distance between the centre-lines of adjacent rows. The second diagonal measurement may be made in a similar way, after turning the array through 90° about an axis perpendicular to and in the centre of the image plane, and the hardness number may then be calculated and displayed automatically.

The alternative way of using the serial output from one complete electronic scan of a two-dimensional photodiode array is precisely as described above for the measurement of superficial area A, except that the array may be held in a fixed position relative to the image of the indentation and mechanical methods of traversal are unnecessary. The incremental area a is here defined as the product of the row pitch and the photodiode pitch in each row of the array, these dimensions being substantially constant in presently-available photodiode arrays as a result of the precision of manufacture using photomechanical techniques.

FIG. 9 illustrates schematically a two dimensional array 100 and (in broken lines) the image 101 of an indentation in a specimen surface 102 formed in an image plane 101(a) in which array 100 is located. 103 schematically represents array scanning circuitry.

We claim:

1. Hardness testing apparatus, for use in assessing dimensions of an indentation formed under controlled conditions in a region of a surface of a specimen whose hardness is to be tested, from which dimensions a hardness value for the specimen can be derived, the apparatus comprising:
   (a) imaging means for illuminating the region of the surface of the specimen in which the indentation is formed and for forming an image of that region in an image plane of the apparatus, in such a manner that areas of the image formed in the image plane that are within the image of the indentation differ in brightness from areas of the image formed in the image plane that are outside the image of the indentation;
   (b) a one-dimensional array of photosensitive elements arranged at the image plane for sensing brightness levels at image areas distributed over the image formed in the image plane and operable to deliver electrical detection signals having electrical levels representative of the brightness levels at the image areas;
   (c) scanning means for causing relative scanning motion between the array and the image of the region of the surface in which the indentation is formed, perpendicularly of the line of the array;
   (d) discrimination circuit means, connected to said one-dimensional array so as to receive said electrical detection signals, for distinguishing those electrical detection signals of electrical levels consistent with their being representative of brightness levels at image areas within the image of the indentation from those electrical detection signals of electrical levels consistent with their being representative of brightness levels at image areas outside the image of the indentation, and for providing discrimination signals of a first level when the received electrical detection signals are of a level consistent with their being representative of brightness at image areas within the image of the indentation, and of a second level when the received electrical detection signals are of a level consistent with their being representative of brightness at image areas outside the image of the indentation; and
   (e) correlation means for receiving the discrimination signals from said discrimination circuit means and for deriving, in dependence upon the correlation of discrimination signals of the first and second levels respectively in relation to the respective different image areas of the image formed in the image plane, an assessment of dimensions of the indentation.

2. Apparatus according to claim 1, wherein said scanning means comprise an array mounting to which the array is fixed and which is traversable perpendicularly of the line of the array, and scanning circuitry operable to derive the electrical detection signals from the respective photosensitive elements of the array and to scan those elements, to provide the electrical detection signals, one after another in a cyclically repeated sequence.

3. Apparatus according to claim 2, wherein said discrimination circuit means comprises a comparator arranged to receive the electrical detection signals from the photosensitive elements of the one-dimensional array and to compare received electrical detection signals with a threshold signal supplied to the comparator, and, in dependence upon the results of the comparison, to provide discrimination signals at either the first level or the second level, and wherein said correlation means comprise a sample-and-hold circuit operable to respond to discrimination signals of the said first level in such a way as to provide a sample output signal of a selected value which is maintained, after the disappearance of discrimination signals of the first level, for a period of time equal to one complete scanning period of the one dimensional array.

4. Apparatus according to claim 3, wherein said correlation means further comprise a gating circuit connected to the sample-and-hold circuit, to receive the sample output signal, and connected to receive measurement signals indicative of displacements of the traversable array mounting and operable to pass on those measurement signals only when the sample output signal has the said selected value, and a measurement circuit arranged and operable to employ the measurement signals passed on by the gating circuit to provide an assessment of dimensions of the indentation.

5. Apparatus according to claim 3, wherein said correlation means further comprise a gating circuit connected to the sample-and-hold circuit to receive the sample output signal, and connected to receive measurement signals indicative of respective consecutive scannings of the one-dimensional array, and operable to pass on those measurement signals only when the sample output value has the selected value, and a measurement circuit arranged and operable to employ the measurement signals passed on by the gating circuit to provide an assessment of dimensions of the indentation.

6. Apparatus according to claim 3, wherein the said discrimination circuit means further comprises a gating circuit, connected to receive the electrical detection signals from the one-dimensional array and the discrimination signals, operable to pass on the electrical detection signals when the discrimination signals have the second level, an averaging circuit connected to receive electrical detection signals passed on by the gating circuit of said discrimination circuit means, and a summation circuit connected to receive a reference level signal provided in said discrimination circuit means and an averaged signal from the averaging circuit, and operable to deliver to the said comparator, as the said threshold signal, the sum of the reference level signal and the averaged signal.

7. Apparatus according to claim 2, wherein said discrimination circuit means comprises a comparator arranged to receive the electrical detection signals from the one-dimensional array and to compare received electrical detection signals with a threshold signal supplied to the comparator, and, in dependence upon the results of the comparison, to provide discrimination signals at either the first level or the second level, and wherein said correlation means comprise a sample-and-hold circuit operable to respond to discrimination signals of the first level in such a way as to provide a sample output signal of selected value which is maintained for a period of time equal to the delay between the scanning of one element of the array and the next, a gating circuit connected to the sample-and-hold circuit, to receive the sample output signal, and connected to receive addressing signals provided in the scanning circuitry for causing the respective elements of the array to be scanned, one element of the array providing a detection signal each time an addressing signal is applied to the array, and operable to pass on those addressing signals only when the said sample output signal has the said selected value, and a counter connected to receive addressing signals passed on by the gating circuit and operable to provide an assessment of dimensions of the indentation in dependence thereupon.

8. Apparatus according to claim 1, comprising an indenter, having a predetermined multifaceted form, and means for impressing the indenter into the surface of the specimen to form the indentation with a multifaceted form complementary to that of the indenter, said imaging means providing light for illuminating the region of the surface of the specimen in which the indentation is formed and being arranged so as to direct the illuminating light therefrom into oblique incidence with that region of the surface, on to the indentation, in such a manner that the illuminating light is specularly reflected from one or more of the facets of the indentation vertically with respect to the surface of the specimen in which the indentation is formed.

9. Apparatus according to claim 8, wherein said indenter is a diamond indenter with a square-based pyramidal form having a semi-angle of 68°.

10. Apparatus according to claim 1, wherein said imaging means are arranged so as to provide light for illuminating the region of the surface of the specimen in which the indentation is formed which is directed into vertical incidence upon that region of the surface.

* * * * *